US006642177B1

(12) United States Patent
Crudden et al.

(10) Patent No.: US 6,642,177 B1
(45) Date of Patent: Nov. 4, 2003

(54) SARCOSLNATES AS GLUFOSINATE ADJUVANTS

(75) Inventors: Joseph J. Crudden, Hudson, NH (US); James E. Steffel, Hamburg, PA (US)

(73) Assignee: Hampshire Chemical Corp., Lexington, MA (US)

( * ) Notice: Subject to any disclaimer, the term of this patent is extended or adjusted under 35 U.S.C. 154(b) by 0 days.

(21) Appl. No.: 10/245,924

(22) Filed: Sep. 18, 2002

Related U.S. Application Data

(63) Continuation of application No. 09/786,567, filed as application No. PCT/US99/21984 on Sep. 22, 1999, now abandoned.
(60) Provisional application No. 60/101,545, filed on Sep. 23, 1998.

(51) Int. Cl.$^7$ .......................... A01N 25/00; A01N 57/02
(52) U.S. Cl. ....................................... 504/206; 504/358
(58) Field of Search ........................................ 504/206

(56) References Cited

U.S. PATENT DOCUMENTS

| | | | |
|---|---|---|---|
| 4,168,963 A | 9/1979 | Rupp et al. | 71/86 |
| 4,400,196 A | 8/1983 | Albrecht et al. | 71/86 |
| 4,552,580 A | 11/1985 | Aldwinckle | 71/3 |
| 5,686,391 A | 11/1997 | Crudden | 504/258 |

OTHER PUBLICATIONS

Crudden, J.J., Abstract No. 1996:216958, N–acyl sarcosinates: Effective ecofriendly adjuvants for pesticide formulation., American Chemical Society Book of Abstracts, 211$^{th}$ ACS National Meeting, New Orleans, LA. Mar. 24–28, 1996.

*Primary Examiner*—S. Mark Clardy

(57) ABSTRACT

N-Acyl sarcosinates, when combined at relatively low concentrations with 2-amino-4-(hydroxymethyl phosphinyl) butanoic herbicide (glufosinate) as an adjuvant, provide for beneficial herbicide formulations exhibiting excellent activity, little or no phytotoxicity (including aquatic toxicity), and low irritancy (including ocular irritancy).

19 Claims, No Drawings

SARCOSLNATES AS GLUFOSINATE ADJUVANTS

The present application is a continuation of U.S. application Ser. No. 09/786,567, filed May 24, 2001 abandoned; which was the National Stage of International Application No. PCT/US99/21984, filed Sep. 22, 1999; which claims the benefit of U.S. Provisional Application Serial No. 60/101,545, filed Sep. 23, 1998.

BACKGROUND OF THE INVENTION

Glufosinate, or 2-amino-4-(hydroxymethyl phosphinyl) butanoic acid and its salts, in particular its monoammonium salt, is represented by the following formula:

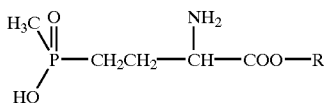

These compounds are selective herbicides, generally used on corn and soybeans resistant to the active ingredient. It is a water-soluble herbicide intended for foliar spray application for the control of a broad spectrum of emerged annual and perennial grass and broadleaf weeds in corn and soybeans. The herbicide is commercially available from AgrEvo USA under the designation "LIBERTY", and is disclosed in U.S. Pat. No. 4,168,963, the disclosure of which is hereby incorporated by reference.

Adjuvants are typically used in formulations to aid the operation or improve the effectiveness of the pesticide, herbicide, etc. The term includes wetting agents, spreaders, emulsifiers, dispersing agents, foaming adjuvants, foam suppressants, penetrants, and correctives. For example, adjuvants such as Valent X-77® Spreader are commonly used to enhance the performance of Fluazifop-P-butyl, another selective herbicide. However, Valent X-77® Spreader and other ethoxylated nonionic surfactants contain free ethylene oxide which may form 1, 4 dioxane, a known carcinogen.

To be effective, glufonsinate must be formulated with a high concentration of surfactant, generally about 110 parts surfactant (such as a tallow amine ethoxylate) to 100 parts of glufosinate active ingredient. Indeed, formulation problems with glufosinate are well known, such as those disclosed in U.S. Pat. No. 4,400,196, the disclosure of which is incorporated by reference. In addition to the cost associated with high concentrations of surfactant, such a high surfactant concentration can cause burning at the axils of the corn leaves under certain conditions.

It is therefore an object of the present invention to provide glufosinate adjuvants and formulations which do not suffer from the drawbacks of the prior art.

It is a further object of the present invention to provide glufosinate formulations with increased activity, lower irritancy and lower toxicity than conventional formulations.

It is yet another object of the present invention to provide glufosinate formulations with relatively low amounts of surfactant compared to conventional formulations.

SUMMARY OF THE INVENTION

The problems of the prior art have been overcome by the present invention, which provides an adjuvant for glufosinate having excellent activity, lower irritancy and lower aquatic toxicity than conventional adjuvants, as well as the resulting formulation. The adjuvant is C8 to C22 sarcosinate or sarcosinate salt, such as sodium cocoyl sarcosinate, sodium lauroyl sarcosinate, the isopropylamine salt of oleoyl sarcosinate, the isopropylamine salt of cocoyl sarcosinate, or combinations thereof, which is combined with glufosinate and provides effective activity at lower concentrations than conventional formulations. The invention also relates to methods of applying effective amounts of the formulation.

DETAILED DESCRIPTION OF THE INVENTION

N-Acyl sarcosinates are mild biodegradable surfactants derived from fatty acid and sarcosine. Typically, sarcosinates are used in the form of their sodium, potassium, ammonium or isopropylamnine salt solution. N-Acyl sarcosinates are produced commercially by the Schotten-Baumann reaction of the sodium salt of sarcosine with the appropriate fatty acid chloride under carefully controlled conditions:

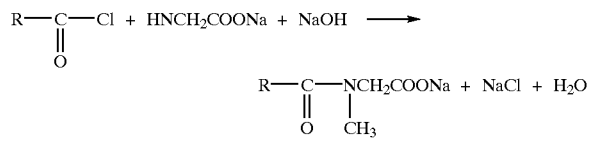

where R is typically a fatty acid of chain length C10 to C18, commonly made from lauric, coconut, palmitic, myristic or oleic acid. After the reaction is complete, the crude sodium salt is acidified to liberate the free fatty sarcosinic acid which is separated from the aqueous by-products. It then is neutralized to a salt form. Sarcosinates such as sodium lauroyl sarcosinate, sodium cocoyl sarcosinate and sodium myristoyl sarcosinate are commercially available under the trademark HAMPOSYL® from Hampshire Chemical Corp., as 30% active solutions in water.

The present inventors have found that C8 to C22 N-acyl sarcosinates, and in particular, the sodium and isopropylamine salts of cocoyl, oleoyl and lauroyl sarcosinate, are excellent adjuvants for glufosinate, in particular, ammonium glufosinate. The sarcosinates are low in toxicity, including aquatic toxicity, low in irritancy, including ocular irritancy, and when combined with glufosinate at relatively low concentrations, result in formulations that exhibit excellent activity with little or no phytotoxicity.

Suitable salts of these sarcosinates that are useful in the present invention include monoethylamine; diethylamine; triethylamine; alkali metal, particularly sodium and potassium, most preferably sodium; isopropylamine; and ammonia or amino alcohols such as tris amino or 2-dimethylamino-2-methyl-1-propanol. A combination of these salts can be used in a glufosinate formulation.

Preferably 30% sarcosinate solutions are used so that the final concentration of sarcosinate in the formulation is from about 4 to about 40 parts of sarcosinate per 100 parts of glufosinate. Higher concentrations can be used, but concentrations within the aforementioned range are preferred in view of the lower overall cost involved and in view of the desire to minimize phytotoxicity. Concentration of from about 4 to about 16 parts of sarcosinate per 100 parts glufosinate are especially preferred for these reasons. The extremely low amounts of sarcosinate concentrations effective as adjuvants for glufosinate is surprising, in view of the conventional wisdom that high concentrations of surfactant are required in order to obtain effective levels of permeation of glufosinate into the plants, for example.

The aqueous formulations can be prepared by first mixing the appropriate sarcosinate with water, and then mixing the glufosinate herbicide with the resulting surfactant solution.

Preferably the formulations of the present invention are applied as foliar spray directly to the plant or to the locus thereof. Thorough coverage is preferred. Preferably the plant is corn or soybean resistant to glufosinate. Application may be in accordance with conventional teachings. For example, in the case of corn, application may be made from emergence of the crop until the corn is 24" tall or in the V-7 stage of growth, i.e., 7 developed collars, whichever occurs first. In the case of soybeans, application may be made from emergence to the bloom growth stage. Application is preferably made when weeds are actively growing.

The invention is further illustrated by the following non-limiting examples.

EXAMPLE 1

The postemergence herbicide glufosinate was added to 30% solutions of sodium cocoyl sarcosinate, isopropylamine cocoyl sarcosinate and isopropylamine oleoyl sarcosinate in various amounts, so that samples were created for each of the foregoing salts in final surfactant concentrations of 4%, 16% and 32%. Liberty Link™ herbicide commercially available from AgrEvo, and glufosinate alone were used as controls. The samples were tested for effectiveness on the glufosinate tolerant field corn variety Pioneer 34A55, planted in a 50/50 mix of Guard's potting soil and topsoil. Seeds were germinated in 4 inch pots and maintained for one month with regular watering and temperatures to simulate field conditions. The plants were transplanted 45 days later to 6 inch pots with one plant per pot. Fertilizer was applied in the form of 20-10-10 at planting to provide 50 lbs. Nitrogen/acre and at transplanting to provide 25 lbs nitrogen/acre. Each treatment was replicated four times in a randomized complete block design. The treatments were applied twenty-six days after transplanting using a syringe to deliver 10 mls into the whorl of each plant. The volume of 10 mls was selected to fill the whorl of the largest plant in the study, all others were filled to running over.

Application rates were selected based on the maximum labeled rate for Liberty 1.67 EC of 28 fluid ounces/acre (0.365 lbs./acre of glufosinate). Based on this registered use pattern, three rates of glufosinate were chosen for this study: (1) 0.365 lbs ai/acre (x); (2) 0.73 1 lbs ai/acre (2x); and (3) 1.461 lbs ai/acre (4x). An application volume of 15 gal.acre was used to determine the mix concentration used.

The three glufosinate rates were compared as the commercial Liberty 1.67 EC formulation and equivalent tank mixes of the surfactant free glufosinate 600EC (5.0 lbs. Ai/gal and sarcosinate surfactant at rates equivalent to the genapol surfactant used in the Liberty 1.67 EC). Using the relationship of 220 g/l of genapol to 200 g/l of glufosinate in the Liberty 1.67 EC formulation, the rate of surfactant is 1 10% of the glufosinate ai in any given treatment.0

Twenty-seven DAT ratings of the % control of the various samples were carried out. The data are shown in Table 1 that follows:

TABLE 1

Effect of Cocoyl and Oleoyl Sarcosinate Salts on the Activity of Glufosinate

| Treatment Name | | Lbs. Adj./JA | Rate lbs. ai/A | % Control 27 Days After Treatment Plant Species | | | | | | |
|---|---|---|---|---|---|---|---|---|---|---|
| | | | | Setia | Porol | Amabl | Polpy | Sotlu | Total | Average |
| Liberty Herbicide | (Note 1) | 0.32 | 0.32 | 93.33 | 71.67 | 81.67 | 90.0 | 90.00 | 426.67 | 85.33 |
| Glufosinate | | 0 | 0.32 | 61.67 | 78.33 | 73.33 | 81.67 | 60.00 | 355.00 | 71.00 |
| Na Cocoyl Sarcosinate | 4% | 0.013 | 0.32 | 100.00 | 76.76 | 93.33 | 63.33 | 100.00 | 453.42 | 90.68 |
| Na Cocoyl Sarcosinate | 16% | 0.051 | 0.32 | 91.67 | 78.33 | 93.33 | 96.76 | 98.33 | 458.42 | 91.68 |
| Na Cocoyl Sarcosinate | 32% | 0.102 | 0.32 | 96.67 | 91.67 | 88.33 | 68.33 | 98.33 | 443.33 | 88.67 |
| IPA Cocoyl Sarcosinate | 16% | 0.051 | 0.32 | 98.33 | 75.00 | 96.67 | 96.67 | 98.33 | 465.00 | 93.00 |
| IPA Cocoyl Sarcosinate | 32% | 0.102 | 0.32 | 61.67 | 51.67 | 66.67 | 61.67 | 56.67 | 298.35 | 59.67 |
| IPA Oleoyl Sarcosinate | 4% | 0.013 | 0.32 | 100.00 | 83.33 | 95.00 | 91.7 | 98.33 | 468.33 | 93.67 |
| IPA Oleoyl Sarcosinate | 18% | 0.051 | 0.32 | 91.67 | 76.67 | 91.67 | 95.00 | 100.00 | 455.01 | 91.00 |
| IPA Oleoyl Sarcosinate | 32% | 0.102 | 0.32 | 96.67 | 86.67 | 93.33 | 98.33 | 85.00 | 460.00 | 92.00 |

Note 1.
Liberty Herbicide applied at 1.67 lbs. Per acre. (Contains about 100 parts surfactant per 100 parts active.)
Plant Species:
Setia = Foxtail., Giant - setaria
Porol = Purslane, Common - *Portulaca oleraca*
Amabl = Pigweed, Prostrate - *Amaranthus blitoides*
Polpy = Smartweed, Pennsylvania - *Polygonium pensylvanicum*
Setiu + Foxtail, Yellow - Sataria Leutescens The compositions of the present invention exhibited superior effects in virtually every concentration tested in the 27 day results, compared to both the commercially available herbicide and glufosinate with no adjuvant, notwithstanding the relatively low amount of surfactant employed.

EXAMPLE 2

Three rates of postemergence herbicide glufosinate in combination with sodium cocoyl sarcosinate, isopropylammonium cocoyl sarcosinate and isopropylammonium oleoyl sarcosinate were compared to equal rates of glufosinate alone and the commercial formulation, LIBERTY 1.67 EC. The test was conducted on the glufosinate tolerant field corn variety Pioneer 34A55, planted on Oct. 21, 1997 in a 50/50 mix of Guard's potting soil and topsoil in Berks County, Pa. Seeds were germinated in 4 inch pots and maintained for one month with regular watering and temperatures to simulate field conditions. The plants were transplanted on Dec. 5, 1997 to 6 inch pots with one plant per pot. Fertilizer was applied in the form of 20-10-10 at planting to provide 50 lbs.

N/acre and at transplanting to provide 25 lbs. N/acre. Each treatment was replicated four times in a randomized complete block design. The treatments were applied on Dec. 31, 1997 using a syringe to deliver 10 ml.—into the whorl of each plant. The volume of 10 ml was selected to fill the whorl of the largest plant in the study, all others were filled to running over.

Application rates were selected based on the maximum labeled rate for LIBERTY 1.67 EC of 28 fluid ounces/acre (0.365 Lbs. ai/acre of glufosinate) and two applications per year (56 fluid ounces of LIBERTY 1.67 EC or 0.731 lbs. ai/acre of glufosinate). An application volume of 15 gal/acre was used to determine the mix concentration used. Using the relationship of 220 g/l of Genapol to 200 g ai/l of glufosinate in the LIBERTY 1.67 EC formulation, the rate of surfactant is 110% of the glufosinate ai in any given treatment.

The treatments were evaluated for phytotoxicity in the form of chlorosis, necrosis and abnormal growth by visually inspecting each plant. When damage was present, each plant was given a damage rating from 0 to 10 with 0 indicating no effect and 10 indicating death.

Results are shown in the following Table:

| Treatment | Rate Lbs al/acre | Ratings 20 days after treatment |
|---|---|---|
| 1) Glufosinate (Active without adjuvant) | 1.46 | 0.8 b |
| 2) Liberty (commercial glufosinate with Genapol 110% on active) | 0.365 | 4.5 a |
| 3) Glufosinate (with Na Cocoyl sarcosinate 110% on the active) | 0.365 | 1.0 b |
| 4) Glufosinate (with isopropylammonium cocoyl sarcosinate 110% on active) | 0.365 | 1.5 b |
| 5) Glufosinate (with isopropylammonium olcoyl sarcosinate 110% on active) | 0.365 | 2.3 b |
| 6) Control (water) | 0.00 | 0.5 b |

Means followed by the same letter do nut significantly differ (P=0.05, Duncan's New MRT).

The efficacy study indicated that 36% N-acyl sarcosinate based nit active level is sufficient adjuvant to ensure control of nuisance weeds. Accordingly, the amount of sarcosinate used in the above study is at a level three times that required for weed control, whereas the LIBERTY herbicide requires 110% Genapol adjuvant based on the active to ensure efficacy. Even at these high levels, the N-acyl sarcosinate showed minimal phytotoxicity.

What is claimed is:

1. A herbicidal composition comprising a herbicidally effective amount of 2-amino-4-(hydroxymethyl phosphinyl) butanoic acid or a salt thereof, and between about 4 parts and about 40 parts, per 100 parts of said butanoic acid or said salt thereof, of an adjuvant comprising an N-acyl sarcosinate or a salt thereof having the formula:

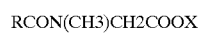

RCON(CH3)CH2COOX wherein R is C8 to C22 alkyl or alkenyl, and X is hydrogen, alkali metal, ammonium, C1–C6 alkylamine or an amino alcohol.

2. The herbicidal composition of claim 1, wherein said 2-amino-4-(hydroxymethyl phosphinyl) butanoic acid is in the form of its isopropylamine salt.

3. The herbicidal composition of claim 1, wherein said N-acyl sarcosinate is selected from the group consisting of alkali metal salts of lauroyl sarcosinate, alkali metal salts of cocoyl sarcosinate, and a mixture of an alkali metal salt of lauroyl sarcosinate and an alkali metal salt of cocoyl sarcosinate.

4. The herbicidal composition of claim 2, wherein said N-acyl sarcosinate is selected from the group consisting of alkali metal salts of lauroyl sarcosinate, alkali metal salts of cocoyl sarcosinate, and a mixture of an alkali metal salt of lauroyl sarcosinate and an alkali metal salt of cocoyl sarcosinate.

5. The herbicidal composition of claim 1, wherein said adjuvant is sodium lauroyl sarcosinate.

6. The herbicidal composition of claim 2, wherein said adjuvant is sodium lauroyl sarcosinate.

7. The herbicidal composition of claim 1, wherein said adjuvant is sodium cocoyl sarcosinate.

8. The herbicidal composition of claim 2, wherein said adjuvant is sodium cocoyl sarcosinate.

9. A herbicidal composition comprising a herbicidally effective amount of 2-amino-4-(hydroxymethyl phosphinyl) butanoic acid or a salt thereof, and between about 4 parts and about 16 parts, per 100 parts of said butanoic acid or said salt thereof, of diethylamine sacosinate.

10. A method of controlling weeds in crop, comprising applying to said crop or the locus thereof an effective amount of a herbicidal composition comprising 2-amino-4-(hydroxymethyl phosphinyl) butanoic acid or a salt thereof and between about 4 parts and about 40 parts, per 100 parts of said butanoic acid or said salt thereof, of an adjuvant comprising an N-acyl sarcosinate or a salt thereof having the formula:

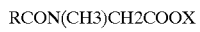

RCON(CH3)CH2COOX wherein R is C8 to C22 alkyl or alkenyl, and X is hydrogen, alkali metal, ammonium, C1–C6 alkylamine or an amino alcohol.

11. The method of claim 10 wherein said 2-amino-4-(hydroxymethyl phosphinyl) butanoic acid is in the form of its isopropylamine salt.

12. The method of claim 10, wherein said adjuvant is sodium lauroyl sarcosinate.

13. The method of claim 11, wherein said adjuvant is sodium lauroyl sarcosinate.

14. The method of claim 10, wherein said adjuvant is sodium cocoyl sarcosinate.

15. The method of claim 11, wherein said adjuvant is sodium cocoyl sarcosinate.

16. The method of claim 10, wherein said adjuvant is present in said herbicidal composition in a concentration of between about 4 and 40%.

17. The method of claim 10, wherein said crop is selected from the group consisting of corn and soybean.

18. The method of claim 10, wherein said herbicidal composition is applied as a foliar spray.

19. A herbicidal composition comprising a herbicidally effective amount of 2-amino-4-(hydroxymethyl phosphinyl) butanoic acid or a salt thereof, and between about 4 parts and about 16 parts, per 100 parts of said butanoic acid or said salt thereof, of ammonium sacosinate.

* * * * *